United States Patent [19]

King-Smith et al.

[11] Patent Number: 4,690,145
[45] Date of Patent: Sep. 1, 1987

[54] OUTPUT LIMITED ELECTRICAL STIMULATOR FOR BIOLOGICAL TISSUE

[75] Inventors: Eric A. King-Smith, St. Louis Park; Walter J. ReMine, St. Paul; Joel R. Dufresne, Vadnais Heights, all of Minn.

[73] Assignee: Minnesota Mining and Manufacturing Company, St. Paul, Minn.

[21] Appl. No.: 745,084

[22] Filed: Jun. 17, 1985

[51] Int. Cl.⁴ ............................................. A61N 1/36
[52] U.S. Cl. ................................................... 128/421
[58] Field of Search ........................ 128/421, 422, 423

[56] References Cited

U.S. PATENT DOCUMENTS

| | | | |
|---|---|---|---|
| 4,126,137 | 11/1978 | Archibald | 128/422 |
| 4,167,190 | 9/1979 | Sorgnson et al. | 128/423 R |
| 4,177,819 | 12/1979 | Kofsky et al. | 128/422 |
| 4,232,679 | 11/1980 | Schulman . | |
| 4,255,790 | 3/1981 | Hondeghem . | |
| 4,390,023 | 6/1983 | Rise . | |
| 4,431,000 | 2/1984 | Butler et al. . | |
| 4,476,869 | 10/1984 | Bihn . | |

FOREIGN PATENT DOCUMENTS 2122904  1/1984  United Kingdom .

OTHER PUBLICATIONS

Buckett et al, "A Flexible Portable Functional Electrical Stimulation System, 36th *ACEMB*, Sep. 12-14, 1983, p. 39.
Hogan, "Neuromuscular Stimulator Permits Customized Therapy", *Design News*, pp. 108-110, Sep. 17, 1984.
Hogan, "TENS Unit Modulates Output to Evade Body's Adaptive Capability", Design News, Sep. 17, 1984, pp. 114-115.

*Primary Examiner*—William E. Kamm
*Attorney, Agent, or Firm*—Donald M. Sell; James A. Smith; William D. Bauer

[57] ABSTRACT

An output limited electrical stimulator for biological tissue. Stimulus parameters, which can be modulated, are used to specify an electrical stimulus signal. A calculation element calculates the electrical charge which would be generated by an electrical stimulus signal defined by the modulated stimulus parameters. A limit element compares the calculated electrical charge against a predetermined standard and adjusts at least one of the stimulus parameters. An electrical stimulus signal is then generated using the adjusted stimulus parameters assuring that the electrical stimulus signal generated will have an electrical charge of not more than the predetermined standard.

3 Claims, 14 Drawing Figures

OUTPUT LIMITED ELECTRICAL STIMULATOR FOR BIOLOGICAL TISSUE

BACKGROUND OF THE INVENTION

The present invention relates generally to electrical stimulators for biological tissue and more particularly to output limited electrical stimulators for biological tissue.

Electrical stimulators providing an electrical stimulus signal are useful for biological tissue. One significant use for electrical stimulators of this type is for transcutaneous electrical nerve stimulation (TENS) which generate carefully controlled electrical stimulus signals which are delivered via suitable electrodes through a patient's skin to underlying biological tissue. The electrical stimulus signals are utilized for masking pain signals, for example, the sensation of pain felt by a patient after surgery. Because the patient's response to transcutaneous electrical nerve stimulation may vary significantly, a wide range of electrical stimulus signals and sets of stimulus parameters for those electrical stimulus signals must be provided. A second use of electrical stimulators is for neuromuscular (NMS) stimulation in order to initiate or control muscular contraction in a patient. Since a wide variety of muscular contractions are available, a wide variety of sets of stimulus parameters must be provided to designate a wide variety of electrical stimulus signals. Such stimulus parameters typically specify the pulse type, pulse amplitude and pulse duration in a pulsatile electrical stimulus system. A set of stimulus parameters or a plurality of sets, uniquely specify an electrical stimulus signal.

While it is desirable to have the electrical stimulus signal applied to biological tissue for transcutaneous electrical nerve stimulation or neuromuscular stimulation, there is some risk of cardiac excitation in the patient or user of the electrical stimulator. For this reason, there are generally acceptable standards relative to the "strength-duration curve" of electrical stimulus signals. Such strength-duration curves specifies the maximum strength of electrical charge which the electrical stimulus signal should be able to generate and pass through the biological tissue load. The electrical charge limit is therefore a known, predetermined standard. The electrical charge limit of the electrical stimulus signal is a function of pulse amplitude, pulse duration and pulse type (wave form).

In the operation of an electrical stimulator, it is often desirable to have the stimulation parameters varied or modulated according to some predetermined algorithm. Such variation is useful to have available the maximum possible range of stimulus parameters to gain the maximum beneficial response to transcutaneous electrical nerve stimulation (TENS) or for adjusting the strength of muscular contraction under varying loads or conditions. One technique for varying the stimulus parameters is to simultaneously specify a maximum value for stimulation parameter such as pulse amplitude and pulse duration and randomly select certain percentages of those maximum values for use in developing the electrical stimulus signal.

When such a stimulus parameter variation requirement is combined with a maximum charge limit requirement, a problem is uncovered. If the maximum charge limit is to be observed simply by selection of maximum values for pulse amplitude and pulse duration, the maximum values to be selected for these stimulus parameters must be below those which would create the maximum charge limit, for any possible combination of stimulus parameter values, even though in practice only a small percentage of the electrical stimulus signals would be above the maximum charge limit due to the random variation of the two stimulus parameters.

SUMMARY OF THE INVENTION

The present invention provides an electrical stimulator which allows the setting of the maximum value of stimulus parameters, such as pulse amplitude and pulse duration, which are subject to variation or modulation according to a predetermined algorithm and which would develop an electrical stimulus signal exceeding the maximum charge limit should the maximum values be utilized. The electrical stimulator utilizes a real time output limit device which looks at the electrical stimulus signal which is to be generated, calculates the electrical charge associated with such an electrical stimulus signal and automatically limits one or more of the stimulus parameters pertaining to that electrical stimulus signal in order to limit the electrical stimulus signal to the maximum charge limits allowed under a preset standard.

Thus, the present invention provides an electrical stimulator for biological tissue having output limits. A storage element is provided for storing a plurality of sets of stimulus parameters designed to specify an electrical stimulus signal having a pulse amplitude and a pulse duration. A calculation element is operatively coupled to the storage element for calculating the electrical charge which would be generated by the electrical stimulus signal developed from the plurality of sets of stimulus parameters. A limit element is operatively coupled to the calculation element for comparing the electrical charge of the electrical stimulus signal with a predetermined standard and for adjusting at least one of the plurality of sets of stimulus parameters so that the electrical charge of the electrical stimulus signal would not exceed the predetermined standard. A generator is operatively coupled to the storage element, to the calculation element and to the limit element, for taking at least one of the sets of stimulus parameters as adjusted by the limit element and generating a series of digital output words indicative of the electrical stimulus signal. Further, the present invention provides a converter operatively coupled to the generator for converting the series of digital output words into the electrical stimulus signal the electrical stimulus signal adapted to be coupled to biological tissue. Thus, the electrical stimulator of the present invention provides an electrical stimulus signal output whose charge limit is at or below a predetermined standard even though the electrical stimulus signal would have exceeded that predetermined standard if the maximum value of all the stimulus parameters had been selected.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Figure 1:
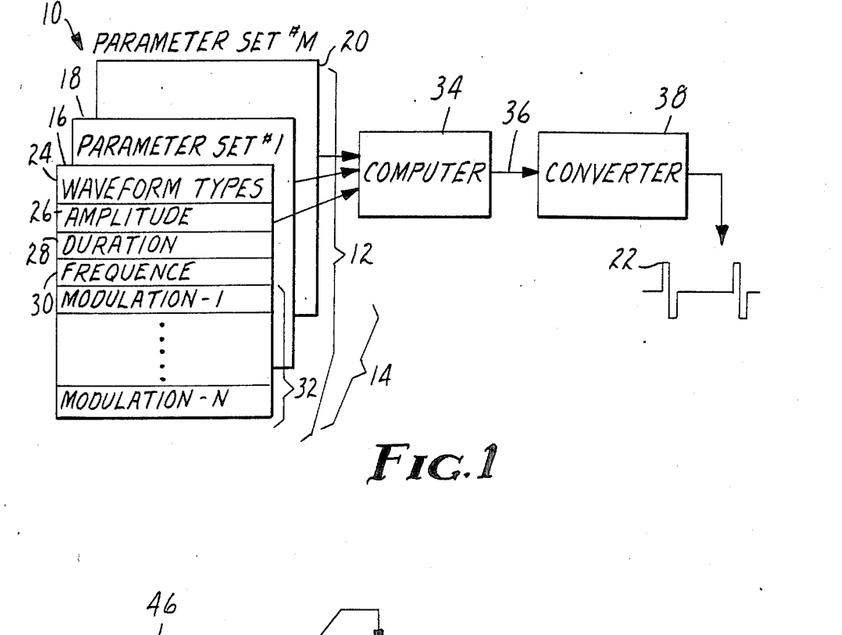
FIG. 1 is a schematic representation of an electrical stimulator of the present invention.

An electrical stimulator 10 embodying the present invention is illustrated in FIG. 1. Storage element 12 contains a plurality of sets of stimulus parameters 14 which are diagramatically illustrated as stimulus parameter set 1 (16), stimulus parameter set 2 (18) through stimulus parameter set M (20). Each of the plurality of stimulus parameters 14 contain information which is designed to define or specify an electrical stimulus signal 22 to be generated by the electrical stimulator 10. An example of the type of stimulus parameters 14 is diagramatically illustrated with respect to parameter set 1 (16) as waveform type 24, pulse amplitude 26, pulse duration 28, pulse frequency or repetition rate 30 and modulation factors 32. While shown diagramatically in FIG. 1 storage element 12 can preferably consist of digital storage memory such as a randomly addressable memory of suitable capacity and structure to hold the data contained within the plurality of sets of stimulus parameters 14.

Computer 34 performs the calculation, limiting and generation functions of the electrical stimulator 10 of the present invention. Computer 34 selects one or more of the plurality of sets of stimulus parameters 14 from storage element 12, calculates the electrical charge which would be generated by the electrical stimulus signal which would be specified from the selected sets of stimulus parameters, compares the electrical charge against a predetermined standard and adjusts at least one of the parameters within the sets of stimulus parameters 14 so that the electrical charge of the electrical stimulus signal would not exceed the predetermined standard and generates a series of digital output words indicative of the electrical stimulus signal to be generated. In general, computer 34 may take the form of any general purpose computing device and in a preferred embodiment is a model 80C49 microcomputer manufactured by Intel Corporation. Detailed operation of the program utilized to operate computer 34 will be described in greater detail below. Converter 38 receives the series of digital output words 36 from the computer 34 and converts the digital output words 36 to a series of time sequenced output current levels which is electrical stimulus signal 22. It is preferable that converter 38 be a highly accurate and linear digital-to-analog output circuit in order to assume accurancy in the computation of the allowable charge limits specified by the stimulus parameters 14. In a preferred embodiment, converter 38 is an output circuit as is described in copending United States patent application filed on the same day as the present application invented by Joel R. Dufresne and Alan P. Dieken, entitled Electrical Stimulator For Biological Tissue Utilizing Linear Current Output Circuit, identified as file number 40008USA1A and assigned to the assignee of the present invention, the contents of which is hereby incorporated by reference.

Figure 2:
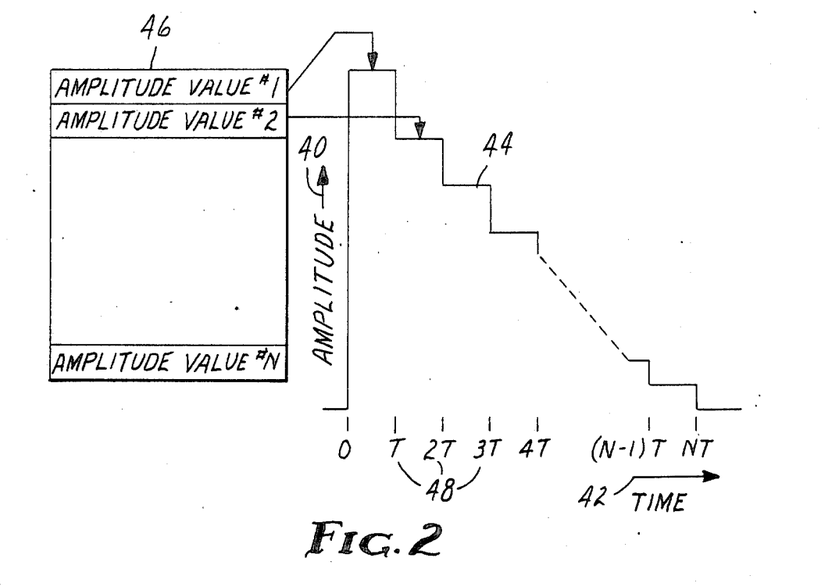
FIG. 2 is a diagram of an exemplary electrical stimulus signal.

The waveforms specified by the digital output words 36 generated by computer 34 are constructed by the computer 34 according to a template stored within computer memory as is illustrated in FIG. 2. As can be seen the diagram has a vertical axis representing pulse amplitude 40 and a horizontal axis representing time 42. A curve 44 is generated utilizing the series of amplitude values 46 which are obtained from the stored waveform template corresponding to the waveform type 24 and stimulus parameters scaled according to pulse amplitude 26. Each step in curve 44 represents a sample period for the electrical stimulus signal 22 to be generated. The duration of the electrical stimulus signal 22 generated is set by the length for the individual sample periods 48, as specified by pulse duration 28. The charge Q supplied by the output stage of converter 38 during an individual pulse can be computed as:

$$Q = \sum_{i=1}^{N} v(i) \times T,$$

where T is the sampling period 48 of the pulse waveform, N is the number of the required samples (length of the template) and V (i) is the output current amplitude during the ith sample period 48. Since the converter 38 contains a linear output stage of known gain, i.e. a specified current output to digital word input, the actual pulse charge Q of the electrical stimulus signal 22 provided by the electrical stimulator 10 will closely approximate the computed value.

Classical studies of nerve/muscle excitation has shown that the stimulating current amplitude threshold is a function of pulse duration. The relationship has become to be known as the "strength-duration curve". Such a "strength-duration curve" has been utilized by the Association for the Advancement of Medical Instrumentation (AAMI) in defining the risk of cardiac excitation when transcutaneous electrical nerve stimulation (TENS) is applied to the body. AAMI has proposed a standard for transcutaneous electrical nerve stimulation in which the maximum pulse charge output, QAAMI, is given by the formula:

$QAAMI = 20 + 0.028 \times D$ microcoulombs, where D is the duration of the pulse in microseconds as defined by its 50% amplitude points. The AAMI standard is the preferred predetermined standard utilized in limiting the charge limit of the electrical stimulation signal 22 of the present invention. It is to be recognized and understood, however, that the AAMI standard is one of but many general standards which could be utilized in the construction of a device according to the present invention.

In the preferred embodiment, the computer 34 of the electrical stimulator 10 computes the charge output yielded by the modulated stimulus parameters 14 each time a modulation algorithm requires a change in pulse amplitude 26, pulse duration 28 or waveform type 24. The need for this continuous checking of stimulus parameters requires efficient computation methods. If the maximum values of pulse amplitude 26 and pulse duration 28 for a given waveform type 24 cannot exceed the charge limit standard then no further charge limit checking and limiting need be performed until the maximum values of pulse amplitude 26, pulse duration 28 or waveform type 24 are changed. However, if for the particular waveform type 24, the maximum value of pulse amplitude 26 and pulse duration 28 would exceed the predetermined charge limit, continuous calculation and limiting of the selected stimulus parameters 14 must be accomplished in order to ensure that the generated electrical stimulus signal 22 does not exceed the charge limit guidelines.

The formula supplied above is for the computation of the charge Q. The sample time T can generally be varied only in integer multiples of the computer's 34 instruction cycle time C. Further, in general, some minimum value of sample time B is possible with the general formula of the sample time T being:

$$T = B + C \times j,$$

where J is 0, 1, 2, ..., M with the value of M depending upon the waveform type 24 and the characteristics of converter 38. Further, the output current amplitude and duration of the pulses of the electrical stimulus signal 22 generally has a limited range due to the power source and output stage limitations of converter 38. In a preferred embodiment of converter 38 a digital-to-analog converter is utilized to convert the digital output words 36 supplied by the computer 34 into analog value which is amplified by linear current amplifier. In this preferred embodiment, v (i) can be computed as:

$$v(i) = k \times G \times X(i) \times h,$$

where G is the gain of the linear current amplifier of converter 38, X(i) is the value stored in the template, H is the gain of the digital-to-analog converter which drives the linear current amplifier, i.e. output voltage divided by digital output word 36 value, and k=0, 1, 2, ..., L is an integer parameter in memory which specifies the peak pulse amplitude utilizing this formula. Therefor Q can be rewritten as:

$$Q = K \times (B + C \times j)G \times H \times \sum_{i=1}^{N} \times (i)$$
$$= K \times Y$$

If the computed value of charge Q exceeds the QAAMI limit then the maximum permissable pulse amplitude of the electrical stimulus signal 22 can be computed as k=QAAMI/Y.

Figure 3A:
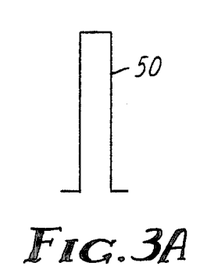
FIG. 3A illustrates a rectangular waveform.
Figure 3B:
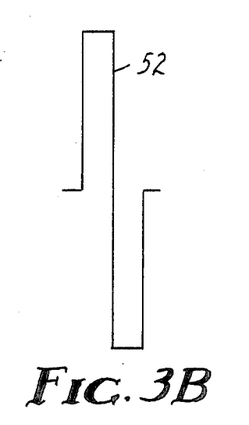
FIG. 3B illustrates a symmetric biphasic waveform.
Figure 3C:
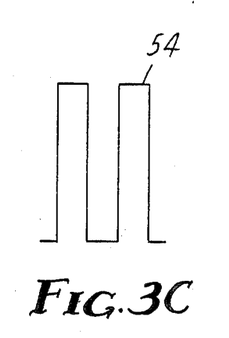
FIG. 3C illustrates a doublet waveform.
Figure 3D:
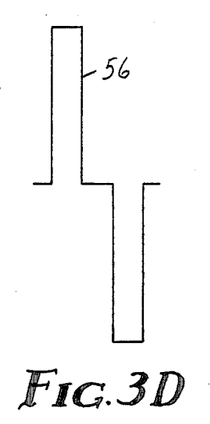
FIG. 3D illustrates an alternating polarity waveform.
Figure 3E:
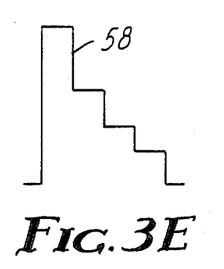
FIG. 3E illustrates a spike waveform.
Figure 3F:
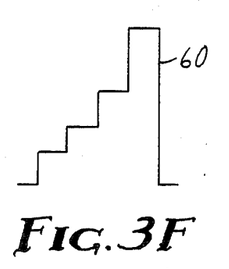
FIG. 3F illustrates an upgoing exponential waveform.
Figure 3G:
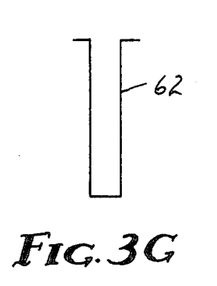
FIG. 3G illustrates an inverse rectangular waveform.
Figure 3H:
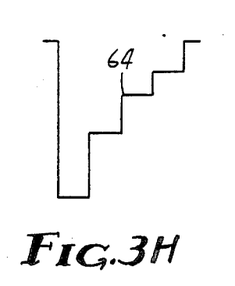
FIG. 3H illustrates an inverse spike waveform.

In a preferred embodiment of the templates stored within computer 34 can take one of the forms illustrated in FIGS. 3A through 3H. For FIG. 3A a rectangular waveform 50 would require M=127 and N=1. In FIG. 3B, symmetic biphasic waveform 52 would require M=64 and N=2. In FIG. 3C, doublet waveform 54 would require M=40 and N=3. In FIG. 3D, alternating polarity waveform 56 would require M=28 and N=3. In FIG. 3E, spike waveform 58 would require M=21 and N=4. In FIG. 3F, upgoing exponential waveform 60 would require M=16 and N=4. In FIG. 3G, inverse rectangular waveform 62 would require M=127 and N=1. In FIG. 3H, inverted spike waveform 64 would require M=21 and N=4. Further, in a preferred embodiment of an implementation of the present invention from the preceding equation the following design values have been determined: B=24.4 microseconds, C=2.44 microseconds, G=43.48 milliamperes/volt, H=0.02 volts and L=127.

In a preferred embodiment, converter 34 has a linear current amplifier whose output requires that the pulse width of electrical stimulus signal 22 be less than 350 microseconds. Given this restriction on pulse widths, and the restrictions on N and M, it is determined that in a preferred embodiment only the rectangular waveform 50 of FIG. 3A the biphasic wave form 52 of FIG. 3B, and the inverted rectangular waveform 62 of FIG. 36 can violate the AAMI charge limit standard. Thus, the remainder of the detailed description of the present invention will be described assuming that only rectangular waveforms 50 and 62 of FIGS. 3A and 3G and biphasic waveform 52 of FIG. 3B can violate the charge limit guide line.

Figure 4:
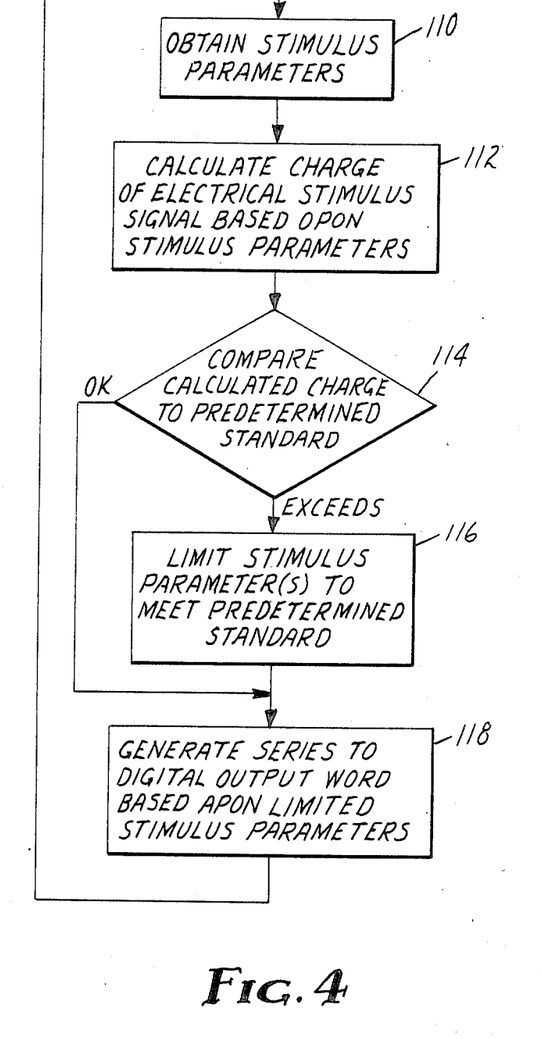
FIG. 4 is a flow chart of the program for the computer of FIG. 1.

The program utilized to operate computer 34 in FIG. 1 is illustrated by the flow chart of FIG. 4. The program at block 110 obtains a set of stimulus parameters 14 from storage element 12. The program at block 112 then calculates the charge of the electrical stimulus signal 22 to be generated based upon the specified pulse parameters and modulated by the predetermined modulation parameters 32 of the set of stimulus parameters 14 utilizing the formula and criteria specified above. Once the charge of the electrical stimulus signal 22 to be generated has been calculated, the calculated charge is compared at block 114 against the predetermined standard, in a preferred embodiment being the AAMI standard. The program at block 116 then operates to limit at least one of the stimulus parameters 14 in order to meet the predetermined standard, in a preferred embodiment the AAMI standard. The program then at block 118 generates a series of digital output words 36 based on the limited stimulus parameters 14 to generate the specified electrical stimulus 22.

Figure 5:
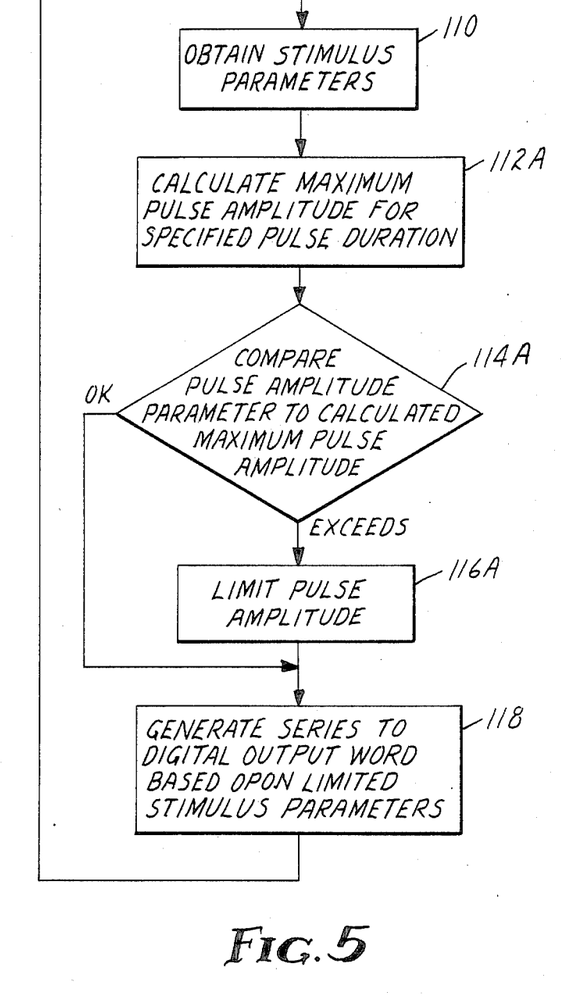
FIG. 5 is a flow chart of a preferred embodiment of the program for the computer of FIG. 1.

An alternative embodiment of a program to be utilized to operate computer 34 of FIG. 1 is illustrated by the flow chart of FIG. 5. The flow chart is similar to the flow chart of FIG. 4. Blocks 112, 114 and 116 have been replaced by blocks 112A, 114A and 116A, respectively. Blocks 112A, 114A and 116A represent an alternative way in the program can accomplish to steps of calculating the electrical charge of the electrical stimulus signal 22, comparing the calculated electrical charge to a predetermined standard and adjusting a stimulus parameter. The program of FIG. 5 operates, at block 112A, by taking the pulse duration 28 specified by the stimulus parameters 14 and calculating the maximum pulse amplitude based upon the predetermined standard and the equations for calculating the electrical charge of the specified waveform type 24. At block 114A, the program compares the calculated maximum pulses amplitude with the specified pulse amplitude 26. If the specified pulse amplitude 26 does not exceed the calculated maximum no adjustment is necessary. If, however, the specified pulse amplitude 26 does exceed the calculated pulse amplitude, the program, at block 116A adjusts, or limits, the specified pulse amplitude 26 to the calculated pulse amplitude.

Figure 6:
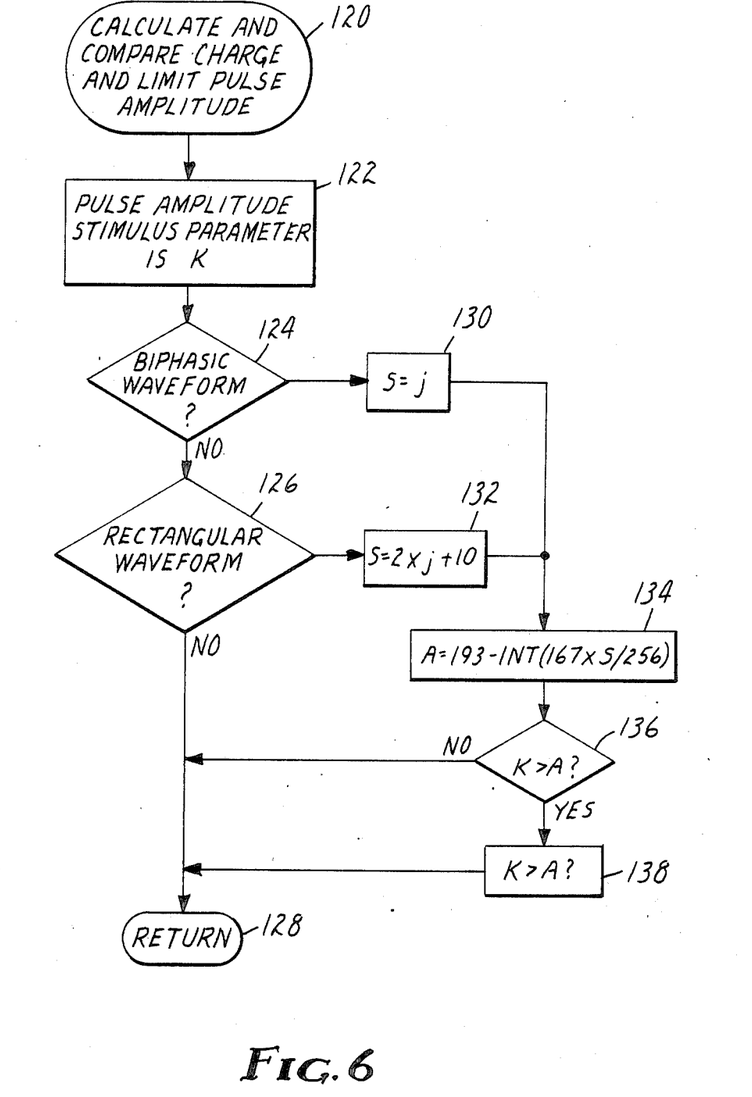
FIG. 6 is a flow chart of a subprogram of the program of FIG. 4.

The calculate, compare and limit processes of blocks 112, 114 and 116 is illustrated in more detail by FIG. 6. The flow chart is entered at block 120 at the time when block 112 in FIG. 4 would be entered. The program at block 122 ascertains the pulse amplitude 26 and specifies this value as k. The program at decision block 124 looks at waveform type 24 to determine if it is a biphasic waveform 52 and at decision block 126 looks at waveform type 24 to determine if it is a rectangular waveform (50 and 62). If not, no calculation of the charge and no limiting of the stimulus parameters needs to be accomplished and the program returns 128 to block 118 of FIG. 4. Should the waveform be either biphasic 52 or rectangular (50 and 62) the charge needs to be calculated based upon the formulas defined above. If the waveform is a biphasic waveform 52 block 130 is entered where S is set equal to j. Alternatively, if the waveform is a rectangular waveform (50 and 62), block 132 is entered where S is set equal to $2 \times j$. The charge calculation is then accomplished according to the formulas provided above which have been simplified according to the preferred embodiment of the present invention at block 134 where A is calculated as 193 $-$ INT ($167 \times S/256$) where INT requires that the quantity within the parentheses be an integer of the value of the calculated amount. Having calculated the charge to be generated by stimulus parameters 14 to form an electrical stimulus signal 22, the program at block 136 inquires whether k is greater than A, A being the preset predetermined standard, in a preferred embodiment the AAMI standard. If the value of the pulse amplitude 26 namely k, is not greater than A, then no limiting is required and the program returns through block 28. If k exceeds A, then pulse amplitude 26 is modified by setting k equal to A the maximum pulse amplitude allowed according to the predetermined standard. The program then returns through block 128.

It is to be recognized and understood that the foregoing description of the calculation of the charge limit has been given with specific detail according to a preferred embodiment utilizing known templates for waveforms as illustrated in FIGS. 3A through 3H and the known characteristics of converter 38. It is to be recognized that other, equally simple, calculations could be made in other embodiments and apparatus to achieve essentially the same advantageous results of the present invention. Further, it is to be noted that the flow chart of FIGS. 5 and 6 operates to limit the maximum charge limit of the electrical stimulus signal 22 by modifying and limiting the pulse amplitude 26. It is to be recognized that one of ordinary skill in the art could also limit the charge by modifying or limiting the pulse duration 26 and/or waveform type 24.

Figure 7:
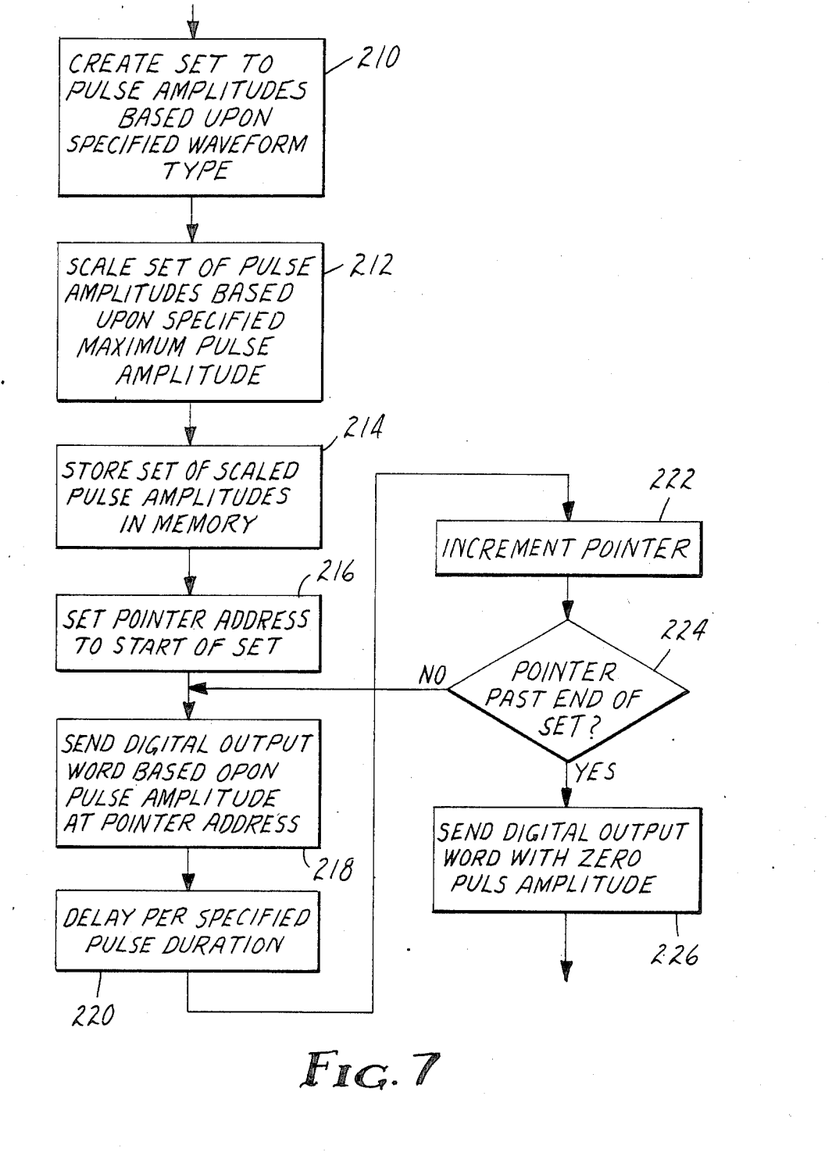
FIG. 7 is a flow chart of a preferred embodiment of the program which generates digital output words.

The portion of the program for computer 34 which generates the series of digital output words 36, block 118 of FIGS. 4 and 5, is illustrated in more detail by the flow chart of FIG. 7. The flow chart of FIG. 7 may be substituted for block 118 of FIGS. 4 and 5 for more detail. The program of FIG. 7 creates at block 210, a set of values, namely pulse amplitude values, based upon the waveform type 24 and the templates of FIGS. 3A through 3H. At block 212, the program scales the set of pulse amplitudes created according to the maximum pulse amplitude specified and stores, at block 214, the set in memory. A pointer address is set equal to the location in memory where the set (or table) of pulses amplitudes starts, block 216. The first digital output word 36, simply a voltage or current amplitude value, sent or outputted to converter 38, block 218. A program is performed based upon the specified pulse duration 28, block 220. As an example, if the waveform type has four steps, i.e. M=4, the delay performed is approximately the actual pulse duration divided by four. The pointer address is incremented, or moved to the next location in memory containing the next of the set of pulse amplitude values (block 222). If (block 224) the pointer is now past the end of the set of pulse amplitudes, then a digital output word 36 with a value of zero is generated (block 226) ending the pulse generation process. If, however, the pointer is still within the range of the set of pulse amplitudes, blocks 218, 220, 222 and 224 are repeated generating the next step or portion of the pulse being generated.

Thus, there has been shown a novel output limited electrical stimulator for biological tissue. It is to be recognized and understood however that various changes, modifications and substitutions in the form and details of the present invention may be made by those skilled in the art without departing from the scope of the following claims.

What is claimed is:

1. An electrical stimulator for biological tissus having output limits, comprising:

storage means for storing a plurality of sets of stimulus parameters designed to specify an electrical stimulus signal comprising a plurality of pulses each having a pulse amplitude and a pulse duration;

calculation means operatively coupled to said storage means for calculating the electrical charge which would be generated by each of said plurality of pulses contained in said electrical stimulus signal from said plurality of sets of stimulus parameters;

limit means having a stored predetermined standard for the maximum electrical charge to be delivered by each of said plurality of pulses, said limit means being operatively coupled to said calculation means for comparing said calculated electrical charge of said electrical stimulus pulse with a predetemined standard and adjusting at least one of said plurality of sets of stimulus parameters so that said electrical charge of said electrical stimulus signal would not exceed said predetermined standard;

generation means operatively coupled to said storage means, to said calculation means and to said limit means for taking at least one of said sets of stimulus parameteres as adjusted by said limit means and generating said electrical stimulus signal as designated by said and of said plurality of sets of stimulus parameters as adjusted.

2. An electrical stimulator as in claim 1 wherein said stimulus parameters include pulse amplitude and pulse duration and wherein said limit means adjusts said at least one of said plurality of sets of stimulus parameters by adjusting said pulse amplitude.

3. An electrical stimulator as in claim 1 wherein calculation means calculates said electrical change whenever a charge in the value of said plurality of sets of stimulus parameters occurs.

* * * * *

UNITED STATES PATENT AND TRADEMARK OFFICE
CERTIFICATE OF CORRECTION

PATENT NO. : 4,690,145

DATED : September 1, 1987

INVENTOR(S) : Eric A. King-Smith, Walter J. Remine and Joel R. Dufresne

It is certified that error appears in the above-identified patent and that said Letters Patent is hereby corrected as shown below:

Col. 1, line 2, "An" should be added to beginning of title.

Col. 6, line 3, "34" should read --38--.

Col. 8, lines 39-40, "predetemined" should read --predetermined--.

Col. 8, line 58, "change" should read --charge--.

Col. 8, line 59, "charge" should read --change--.

Signed and Sealed this

Twenty-sixth Day of July, 1988

Attest:

DONALD J. QUIGG

Attesting Officer

Commissioner of Patents and Trademarks